United States Patent [19]

Beck et al.

[11] Patent Number: 4,495,195

[45] Date of Patent: Jan. 22, 1985

[54] XANTHINE OXIDASE INHIBITING 3(5)-PHENYL-SUBSTITUTED-5(3)-PYRAZOLE-CARBOXYLIC ACID DERIVATIVES, COMPOSITIONS, AND METHODS OF USE

[75] Inventors: James R. Beck; Robert P. Gajewski, both of Indianapolis; Ronald E. Hackler, Greenfield, all of Ind.

[73] Assignee: Eli Lilly and Company, Indianapolis, Ind.

[21] Appl. No.: 437,994

[22] Filed: Nov. 1, 1982

[51] Int. Cl.$^3$ ................ A61J 31/415; C07D 231/20; C07D 49/18

[52] U.S. Cl. .................................... 514/406; 546/278; 548/375; 548/377; 548/378; 514/407

[58] Field of Search ............... 548/374, 375, 378, 377, 548/358; 424/273 P; 546/278

[56] References Cited

U.S. PATENT DOCUMENTS

| | | |
|---|---|---|
| 3,254,093 | 5/1966 | Garbwerke . |
| 3,895,027 | 7/1975 | Katner . |
| 3,899,508 | 8/1975 | Katner . |
| 3,903,106 | 9/1975 | Katner et al. . |
| 4,134,987 | 1/1979 | Huppatz . |
| 4,214,090 | 7/1980 | Huppatz . |
| 4,245,106 | 1/1981 | Brannigan et al. ................. 548/378 |
| 4,346,097 | 9/1980 | Schweiss et al. . |

FOREIGN PATENT DOCUMENTS

| | | |
|---|---|---|
| 704290 | 9/1966 | Belgium . |
| 8439588 | 5/1975 | Belgium . |
| 843959 | 5/1975 | Belgium . |
| 2144568 | 9/1971 | Fed. Rep. of Germany . |
| 2508934 | 4/1974 | Fed. Rep. of Germany . |
| 2410653 | 6/1974 | Fed. Rep. of Germany . |
| 2701091 | 1/1976 | Fed. Rep. of Germany . |
| 43-7300827 | 9/1968 | Japan . |
| 45-4028510 | 11/1970 | Japan . |
| 7112377 | 10/1972 | Netherlands . |

OTHER PUBLICATIONS

Chemical Abstracts, vol. 23, 3704–3705.
Chemical Abstracts, vol. 28, 2003–2004.
Chemical Abstracts, vol. 28, 765–766.
Chemical Abstracts, vol. 29, 7977.
Ber. 60B, 1730–1736 (1927).
Chemical Abstracts, vol. 49, 10936–10938.
Chemical Abstracts, vol. 21, 3903–3904.
Chemical Abstracts, vol. 55, 18752.
J.C.S. Perkin Transactions I, 1383, 2633 (1974) Grimshaw and coworkers.
Chem. Ber., Capuano et al., 112, 3753 (1979).
EP 53,698 and EP 53,678.
J. Org. Chem., 31, 1878 (1966) Tensymeyer et al.
Tetrahedron Letters, No. 19, pp. 1591–1592 (1971), Farkas and Fleglove.

Primary Examiner—Henry R. Jiles
Assistant Examiner—J. G. Mullins
Attorney, Agent, or Firm—James L. Rowe; Arthur R. Whale

[57] ABSTRACT

Aryl pyrazole carboxylic acids and derivatives thereof, are xanthine oxidase inhibitors in vivo.

45 Claims, No Drawings

XANTHINE OXIDASE INHIBITING 3(5)-PHENYL-SUBSTITUTED-5(3)-PYRAZOLE-CARBOXYLIC ACID DERIVATIVES, COMPOSITIONS, AND METHODS OF USE

SUMMARY OF THE INVENTION

This invention provides a method for lowering blood urate levels in mammals having elevated blood urate levels comprising the administration to such a mammal of a dose effective to lower blood urate levels of a pyrazole drug of the formulas:

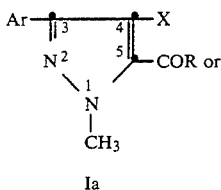

Ia

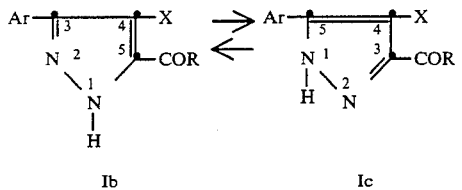

Ib  Ic wherein Ar is pyridyl, thienyl or

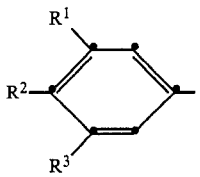

wherein
$R^1$, $R^2$ and $R^3$ are individually H, $C_{1-3}$ haloalkyl, F, Br, Cl, I, $C_{1-3}$ alkyloxy, $R^1$ and $R^2$ or $R^2$ and $R^3$ taken together represent methylenedioxy, provided at least one of $R^1$, $R^2$ and $R^3$ is H, one of $R^1$, $R^2$ and $R^3$ is other than H and only one of $R^1$, $R^2$ and $R^3$ can be I;
R is OH, OM, $NH_2$, NHalk, $N(alk)_2$, Oalk or N-alken-$N(alk)_2$
X is $NH_2$, OH, H, F, Cl, Br, I or $C_{1-3}$ alkyl; alk is $C_{1-5}$ alkyl; alken is $(CH_2)_2$ or $(CH_2)_3$; and M is a nontoxic cation.

In the above formulas, Ib and Ic represent a chemical compound which exists as a tautomeric pair, a 3-aryl-pyrazole-5-carboxylic acid and a 5-arylpyrazole-3-carboxylic acid. Naming of a single tautomer includes the other throughout this specification. When one or more of $R^1$, $R^2$ or $R^3$ are $C_{1-3}$ haloalkyl derivatives it is preferred that such group be fully halogenated such as in a trifluoromethyl or pentachloroethyl group. This fully halogenated alkyl radical is more stable than partially-halogenated haloalkyl radicals and maintain their structural integrity during most synthetic procedures.

One preferred group of pyrazoles useful in the novel methods of this invention are those according to Ia, Ib, Ic in which Ar is substituted phenyl, in particular 3 or 4-trifluoromethylphenyl, 3 or 4-chlorophenyl, 3 or 4-bromophenyl or 3 or 4-methoxyphenyl. Compounds in which Ar is 3-trifluoromethylphenyl constitute a particularly preferred group of novel compounds. A second preferred group of drugs useful in the therapeutic methods of this invention are those in which X is H, OH or $NH_2$, particularly more in which X is H. Thirdly, we prefer to employ the free acids (R=OH) or pharmaceutically-acceptable salts thereof (M is a non-toxic cation) as the active drug in our anti-gout treatment methods).

While all drugs according to formulae Ia, Ib and Ic are active in lowering blood urate levels when administered orally, only those drugs in which R is OH or OM are active parenterally.

A second aspect of this invention provides pharmaceutical formulations which contain as an active ingredient a 3-aryl-5-pyrazole derivative of formula Ia, Ib or Ic, or a pharmaceutically-acceptable salt thereof, associated with one or more pharmaceutically-acceptable carriers, diluents or excipients therefor.

The term "$C_{1-5}$ alkyl" as used herein includes such radicals as methyl, ethyl, n-propyl, isopropyl, n-butyl, isobutyl, sec-butyl, 1-pentyl, 2-pentyl, 3-pentyl, 3-methyl-1-butyl, 3-methyl-2-butyl and the like. The term "$C_{1-3}$ alkyl" as used herein, constitutes a subset of the term "$C_{1-5}$ alkyl" and includes methyl, ethyl, n-propyl and isopropyl.

The term "$C_{1-3}$ haloalkyl" represents halogenated derivations of the $C_{1-3}$ alkyl radicals listed above and includes such radicals as trifluoromethyl, trichloromethyl, difluoromethyl, chlorodifluoromethyl, bromomethyl, $\alpha,\alpha$-difluoroethyl, pentafluoroethyl, heptafluoro-n-propyl, pentachloroethyl, iodomethyl, etc.

Preferred pharmaceutically-acceptable salts useful in our novel methods and formulations are those formed with a non-toxic cation, preferably an alkali metal cation such as K or Na, an alkaline earth metal cation such as Mg or Ca, another non-toxic metal cation such as Al or Zn or a non-toxic metalloid cation such as $NH_4^+$, piperazinium or 2-hydroxyethylammonium.

The compounds of formulas Ia, Ib or Ic may be administered orally to a mammal having high urate blood concentrations and in need of treatment, the active ingredient being mixed with pharmaceutically-acceptable carriers, diluents or excipients as appropriate and being administered in unit dosage forms such as in a tablet or capsule. Each dosage unit should contain the active ingredient in an amount from 2 to 20 mg/kg of mammalian body weight.

For parenteral administration, the drug is usually compounded in unit dosage form as a sodium or potassium carboxylate salt (R=OM and M is K or Na) in an isotonic solution. Such isotonic solutions are particularly adapted for iv or intraperitoneal injection. Parenteral intramuscular injection may be employed either using the free acid or a non-toxic, non-irritating salt thereof plus one or more of the usual pharmaceutical excipients used with intramuscular injections.

However, it is preferred to administer compounds of formula Ia, Ib and Ic by the oral route. For such purpose, either the solid free acid or a pharmaceutically-acceptable salt thereof is preferably employed. In addition, we have discovered that compounds according to the above formula which are not acids or salts; i.e. amides or esters, can be employed as precursors of the free acid since such acid derivatives are often hydrolyzed to the free acid at the pH of the stomach, or by various intracellular hydrolytic enzymes. However, such hydrolytic processes apparently do not always proceed to completion, and the esters and amides of the pyrazolecarboxylic acids represented by formulas Ia, Ib or Ic above are not as active anti-gout drugs on a weight for weight basis as are the free acids or the non-toxic cationic salts thereof. For oral administration, the free acid or a cationic salt thereof in solid form can be mixed with starch and/or other pharmaceutical excipients and the mixture loaded into telescoping gelatin capsules such that each capsule contains a dosage unit of from 100 to 500 mg. of a compound according to the above formulas. Alternatively, starch, a binder, various lubricants, etc. can be mixed together and the mixture compressed into tablets such that each tablet contains a unit dosage having from 100 to 250 or even 500 mg. of a compound of the above formulas. Such tablets can be scored so that half and quarter doses can be administered if desired.

Compounds particularly useful in accordance with the processes and formulations of the invention in the form of their free acid, or salt thereof, include the following:

1-methyl-3-(2-thienyl)-4-aminopyrazole-5-carboxylic acid, sodium salt
1-methyl-3-(4-fluorophenyl)-4-chloropyrazole-5-carboxylic acid
1-methyl-3-(3-iodophenyl)-pyrazole-5-carboxylic acid, calcium salt
1-methyl-3-(4-tolyl)-4-methylpyrazole-5-carboxylic acid, ammonium salt
1-methyl-3-(3-ethylphenyl)-4-hydroxypyrazole-5-carboxylic acid, potassium salt
3(5)-(3-pyridyl)-4-chloro-pyrazole-5(3)-carboxylic acid, magnesium salt
3(5)-(3-thienyl)-4-fluoropyrazole-5(3)-carboxylic acid, tetramethylammonium salt
1-methyl-3-(3-anisyl)-4-bromopyrazole-5-carboxylic acid
1-methyl-3-(3,4-dimethoxyphenyl)-4-chloropyrazole-5-carboxylic acid, aluminum salt
1-methyl-3-(3,5-dimethoxyphenyl)-4-aminopyrazole-5-carboxylic acid, calcium salt
3(5)-(3-chloro-4-methylphenyl)pyrazole-5-(3)-carboxylic acid, magnesium salt
1-methyl-3-(3,4-difluorophenyl)-4-aminopyrazole-5-carboxylic acid
1-methyl-3-(4-trifluoromethyl-3-fluorophenyl)-4-hydroxypyrazole-5-carboxylic acid
3(5)-(3,4-methylenedioxyphenyl)-4-hydroxypyrazole-5(3)-carboxylic acid
3(5)-(4-ethylphenyl)-4-aminopyrazole-5(3)-carboxylic acid, tetraethylammonium salt
3(5)-(4-trifluoromethylphenyl)pyrazole-5(3)-carboxylic acid and the like.

As previously stated, a preferred group of compounds coming within the scope of the above formula, which compounds are not only unexpectedly active as xanthine oxidase inhibitors, but are also novel compositions of matter are those in which Ar is 3-trifluoromethylphenyl. Illustrative of this preferred group of compounds are the following:

1-methyl-3(3-trifluoromethylphenyl)pyrazole-5-carboxylic acid
1-methyl-3-(3-trifluoromethylphenyl)-4-fluoropyrazole-5-carboxylic acid, sodium salt
3(5)-(3-trifluoromethylphenyl)-4-chloropyrazole-5(3)-carboxylic acid, ammonium salt
1-methyl-3-(3-trifluoromethylphenyl)-4-iodopyrazole-5-carboxylic acid, potassium salt
3(3-trifluoromethylphenyl)-4-aminopyrazole-5-carboxylic acid, calcium salt
3(5)-(3-trifluoromethyl-4-fluorophenyl)-4-fluoropyrazole-5(3)-carboxylic acid
3(5)-(3-trifluoromethylphenyl)-4-hydroxypyrazole-5(3)-carboxylic acid, magnesium salt
1-methyl-3-(3-trifluoromethyl-4-methoxyphenyl)-4-hydroxypyrazole-5-carboxylic acid, zinc, salt; and the like.

Precursor compounds, those esters and amides according to I above which are transformed in the stomach or elsewhere after oral administration to carboxylic acids, include the following;

methyl 1-methyl-3-(3-trifluoromethylphenyl)pyrazole-5-carboxylate
N,N-dimethyl-1methyl 3-(4-chlorophenyl)-4-hydroxypyrazole-5-carboxamide
ethyl 1-methyl-3-(4-trifluoromethylphenyl)-4-aminopyrazole-5-carboxylate
N-ethyl-1-methyl 3-(4-iodophenyl)-4-chloropyrazole-5-pyrazolecarboxamide
3(5)-(3,5-xylyl)-4-bromopyrazole-5(3)-carboxamide
1-methyl 3-(3,4-dimethoxy)-4-fluoropyrazole-5-carboxamide It will be apparent that other carboxylic acid derivatives in addition to esters, amides or lower alkylamides, can serve as precursors for the corresponding pyrazolecarboxylic acid upon oral administration; i.e., these carboxylic acid derivatives can be converted by the acid of the stomach (pH≅2), or by enzymatic hydrolysis in other parts of the body, to the free carboxylic acid.

It will also be apparent to those skilled in the art that, upon oral administration of a pyrazolecarboxylic acid, salt or precursor ester or precursor amide thereof, the greater percentage of the pyrazolecarboxylic acid will exist in the stomach in the unionized form; that is to say, the strong acid of the stomach, HCl at pH≅2 will suppress the ionization of the weaker pyrazolecarboxylic acid according to the formula $$Ks = \frac{[H^+] \text{ [pyrazolecarboxylate ion]}}{\text{[pyrazolecarboxylic acid]}}$$

where Ks is the apparent dissociation constant for the particular pyrazolecarboxylic acid.

The compounds of this invention may be prepared according to one or more of the following procedures.

The compounds represented by Ia, Ib or Ic wherein X is H or alkyl and R is other than OH or OM are readily prepared by condensing a benzoyl pyruvic acid ester or amide (II) with hydrazine or methylhydrazine according to Flow Chart 1.

Flow Chart 1

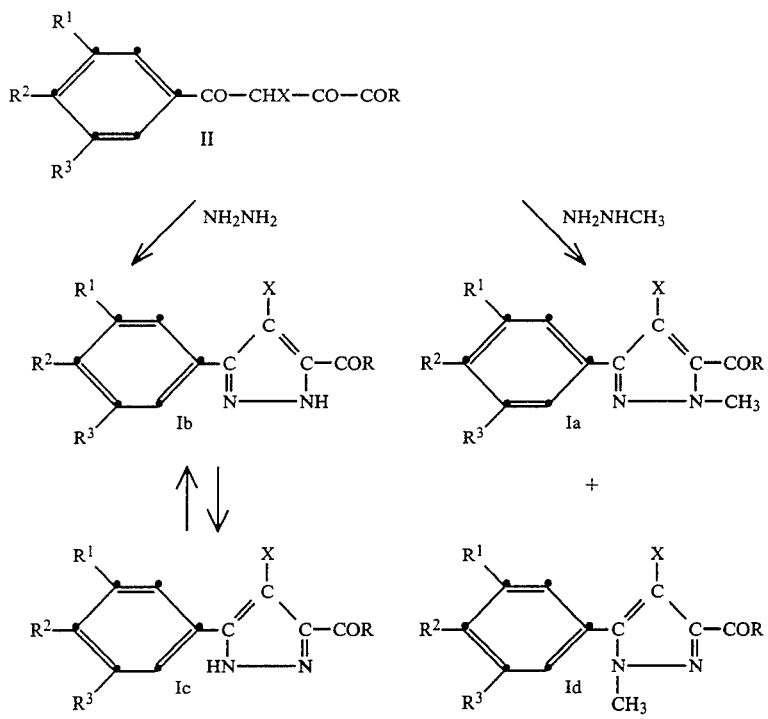

wherein alk, $R^1$, $R^2$ and $R^3$ have their previously assigned significance, X is H or $C_{1-3}$ alkyl and R is Oalk, $NH_2$, NHalk, or $N(alk)_2$. Products Ib and Ic represent a tautomeric equilibrium useful in the therapeutic processes and formulations of this invention, but products Ia and Id represent an isomeric mixture, only one component of which, represented by Ia, is an active anti gout drug. The isomeric mixture is readily separated into its component parts by chromatography, fractional crystallization or other known isomer separation procedure.

Compounds according to Ia and Id, a mixture of isomers, can also be prepared by methylating the tautomeric mixture, Ib and Ic with methyliodide, dimethylsulfate etc.

The starting benzoyl pyruvate esters are readily prepared by a Claisen condensation procedure involving a permissibly-substituted acetophenone and an oxalate ester in the presence of sodium ethylate or the like base.

Useful drugs for the purposes of this invention, and our preferred embodiment—those compounds according to Ia, Ib or Ic in which R is OH—are conveniently prepared from the above compounds wherein R is $OC_{1-5}$ alkyl by basic or acidic hydrolysis, basic hydrolysis being preferred.

Compounds according to Ia, Ib or Ic in which X is halogen and R is OH are conveniently prepared by the action of, for example, molecular chlorine or bromine (where X is to be Br or Cl) on the corresponding ester derivative, Ia, Ib or Ic in which R is Oalk and X is H, followed by basic hydrolysis of the halogenated ester to the free pyrazole-5-carboxylic acid. Iodination at C-4 of the pyrazole-5-carboxylic acid ester can be accomplished with molecular iodine, ICl or other suitable iodinating agent.

The 4-amino derivatives (X is $NH_2$ in Ia, Ib or Ic) are prepared by nitrosating a benzoylpyruvate ester (II in Flow Chart 1) with $N_2O_3$. The resulting derivative, after hydrogen shift, is an oximino derivative III

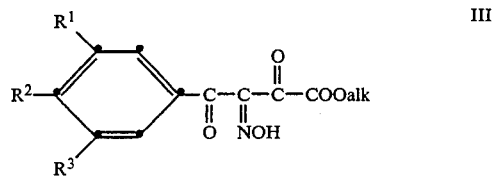

Condensation of the oximino derivative with hydrazine or methyl hydrazine yields compounds according to Ia, Ib, Ic or Id in which X is NO and R is Oalk. Reduction of this thus-prepared 4-nitroso compound with sodium dithionite or similar reducing agent yields directly the 4-aminopyrazole-5-carboxylate ester (after removal of the Id isomer) which is readily hydrolysed to the preferred 5-carboxylic acid.

Finally, the preparation of the 4-hydroxy derivative (X=OH) is illustrated below in Flow Chart 2.

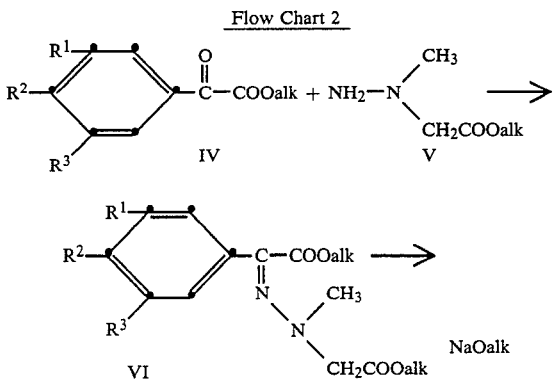

-continued
Flow Chart 2

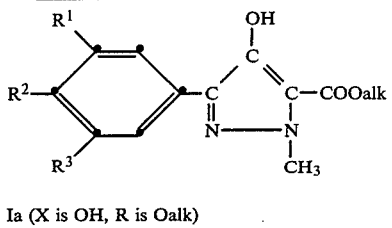

Ia (X is OH, R is Oalk)

According to Flow Chart 2, a benzoyl formate (IV) is reacted with N-methyl-N-alkoxycarbonylmethylhydrazine (V) to yield the N-methyl-N-alkoxycarbonylmethylhydrazone of a benzoylformate (VI). Cyclization of the hydrazone with an alkoxide in a lower alkanol yields a 1-methyl-3-(permissibly substituted phenyl)-4-hydroxypyrazole-5-carboxylic acid alkyl ester which can readily be converted to the corresponding carboxylic acid by base hydrolysis.

Alternatively, the hydrazine employed can be an N-methyl-N-carboxylmethylhydrazine

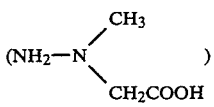
Va which yields the 4-hydroxypyrazole-5-carboxylic acid on cyclization. Similarly, compounds according to Ib or Ic are prepared by using a hydrazine of the formula NH$_2$—NH—CH$_2$—COOalk (Vb) or of the formula NH$_2$—NH—CH$_2$—COOH (Vc) in place of the N-methylhydrazines disclosed above.

This invention is further illustrated by the following specific examples.

EXAMPLE 1

Preparation of 3(5)-(3-trifluoromethylphenyl)pyrazole-5(3)-carboxylic acid

A reaction mixture was prepared from 5.8 g. of ethyl 3-trifluoromethylbenzoylpyruvate and 0.64 g. of hydrazine in 50 ml. of ethanol. The reaction mixture was heated at about 80° C. for about 30 minutes. Water was then added and the reaction mixture cooled. A solid comprising ethyl 3(5)-(3-trifluoromethylphenyl)-pyrazole-5(3)carboxylate was separated and was collected by filtration. Recrystallization of the filter cake from a benzene/hexane solvent mixture yielded crystalline material melting at about 84°–96° C.

The ethyl ester was hydrolyzed without further purification as follows. Ethyl 3(5)-(3-trifluoromethylphenyl)pyrazole-5(3)carboxylate (3.4 g.) was dissolved in 20 ml. of ethanol to which was added 0.5 g. of sodium hydroxide dissolved in 100 ml. of water. The hydrolysis mixture was heated at about 80° C. for about 3 hours and was then cooled. The cooled reaction mixture was made acidic by the addition of 1N aqueous hydrochloric acid and the free acid, which precipitated, was collected by filtration. Recrystallization of the collected free acid from ethanol yielded 3(5)-(3-trifluoromethylphenyl)pyrazole-5(3)carboxylic acid melting at 251°–4° C. having the following elemental analysis.

Theory: C, 51.56; H, 2.73; N, 10.94. Found: C, 51.77; H, 2.64; N, 11.21.

EXAMPLE 2

Preparation of 1-methyl-3-(4-trifluoromethylphenyl)pyrazole-5-carboxylic acid

Following the procedure of Example 1, 18.6 g. of ethyl 4-trifluoromethylbenzoylpyruvate and 3.5 ml. of methyl hydrazine were dissolved in methanol and the mixture heated to refluxing temperature overnight. The solvent was removed in vacuo and the residue dissolved in methylene dichloride. The methylene dichloride solution was chromatographed over silica. Two major fractions were collected. The faster moving material was methyl 1-methyl-3-(4-trifluoromethylphenyl)-pyrazole-5-carboxylate. Fractions containing this material were combined and the solvent removed therefrom. The residue was recrystallized from hexane to melt at 81°–3° C.

Analysis Calculated: C, 54.93; H, 3.90; N, 9.86. Found: C, 54.66; H, 4.02; N, 9.68.

Still following the procedure of Example 1, 6.8 g. of methyl 1-methyl-3-(4-trifluoromethylphenyl)pyrazole-5-carboxylate dissolved in 100 ml. of methanol was heated for about one hour with a solution of 1 g. of sodium hydroxide in 75 ml. of water. The reaction mixture was cooled and then acidified with 1N aqueous hydrochloric acid. The free acid, being insoluble in the acidic solution, separated and was collected by filtration. Recrystallization from benzene yielded 1-methyl-3-(4-trifluoromethylphenyl)pyrazole-5-carboxylic acid melting at 230°–2° C.

Analysis Calculated: C, 53.34; H, 3.36; N, 10.37. Found: C, 53.08; H, 3.32; N, 10.08.

EXAMPLE 3

Preparation of 1-methyl-3-(3-trifluoromethylphenyl)pyrazole-5-carboxylic acid

Following the procedure of Example 1, 5.8 g. of ethyl 3-trifluoromethylbenzoylpyruvate and 0.92 g. of methyl hydrazine were heated in ethanol solution for about one hour at about 80° C. The reaction mixture was cooled and water added. The aqueous mixture was extracted with two 100 ml. portions of ether followed by one 100 ml. portion of chloroform. The combined extracts were dried with phase separation paper. The solvents were removed from the filtrate. NMR indicated that the residue comprised the isomeric pair ethyl 1-methyl-3-(3-trifluoromethylphenyl)pyrazole-5-carboxylate and ethyl 1-methyl-5-(3-trifluoromethylphenyl)pyrazole-3-carboxylate in about a 60–40 mixture. Following the procedure of Example 2, the isomers were separated by chromatography over silica gel using dichloromethane. The faster moving fraction, comprising the desired ethyl 1-methyl-3-(3-trifluoromethylphenyl)pyrazole-5-carboxylate, was collected and the solvent removed therefrom; weight=2.0 g. The desired ethyl ester was hydrolyzed without further purification according to the following procedure. A solution of 2.0 g. of ethyl 1-methyl-3-(3-trifluoromethylphenyl)pyrazole-5-carboxylate in 40 ml. of ethanol was refluxed with a solution of 0.3 g. of sodium hydroxide in 120 ml. of water for about 2 hours. The hydrolysis mixture was cooled and then acidified with 1N aqueous hydrochloric acid. The free acid, being insoluble in the acidic aqueous solution, precipitated and was collected by filtration. Recrystallization of the filer cake yielded 1-methyl-3-(3- trifluoromethylphenyl)pyrazole-5-carboxylic acid melting at 198°-9° C. after recrystallization from ethanol.

Analysis Calculated: C, 53.34; H, 3.36; N, 10.37. Found: C, 53.17; H, 3.49; N, 10.45.

An alternative separation of pyrazole isomers can be achieved by fractional crystallization, illustrated in the following example. 5.5 Grams of methyl 3-trifluoromethylbenzoylpyruvate and 0.92 g. of methyl hydrazine were stirred in 20 ml. of glacial acetic acid for about 3 hours with gentle heating (not exceeding 45° C.). The reaction mixture was poured into an ice-water mixture and 5.5 g. of a white solid collected. This solid was shown by nmr to be a nearly 3:1 mixture of methyl 1-methyl-3-(3-trifluoromethylphenyl)pyrazole-5-carboxylate and methyl 1-methyl-5-(3-trifluoromethylphenyl)-3-carboxylate. This mixture was dissolved in 125 cc. of hot hexane. The hexane solution was filtered and then cooled to 40°. The supernate was decanted from a brown oil and then cooled to $-10°$. Two and one-half grams of white crystals, shown by nmr to contain 98% of the desired 5-carboxylate isomer were obtained.

EXAMPLE 4

Preparation of
1-methyl-3-(4-bromophenyl)pyrazole-5-carboxylic acid

Following the procedure of Example 2, 15.1 g. of methyl 4-bromobenzoylpyruvate and 2.9 ml. of methyl hydrazine were heated to refluxing temperature overnight in methanol solution. Removal of the volatile constituents from the reaction mixture yielded a pair of isomeric N-methyl pyrazoles which were separated as in Example 2 by chromatography over silica gel using methylene dichloride as the eluting solvent. Fractions containing the more rapidly moving constituent, methyl 1-methyl-3-(4-bromophenyl)pyrazole-5-carboxylate, were collected and the solvent evaporated therefrom. Recrystallization of the residue from hexane yielded crystals melting at 121°-3° C.

Analysis Calculated: C, 48.84; H, 3.76; N, 9.49. Found: C, 48.75; H, 3.68; N, 9.41.

Following the procedure of Example 1, the separated isomer, methyl 1-methyl-3-(4-bromophenyl)pyrazole-5-carboxylate (4.5 g. in 100 ml. of ethanol) was hydrolyzed with aqueous sodium hydroxide (0.6 g. of sodium hydroxide in 50 ml. of water). The hydrolysis mixture was heated for about two hours at about 80° C. and was then cooled. Acidification of the hydrolysis mixture with 1N aqueous hydrochloric acid yielded the insoluble free acid which was collected by filtration. Recrystallization of the free acid from ethanol yielded 1-methyl-3-(4-bromophenyl)pyrazole-5-carboxylic acid melting at 255°-7° C. (with decomposition); yield=3.0 g.

Analysis Calculated: C, 47.00; H, 3.23; N, 9.97. Found: C, 46.79; H, 3.03; N, 9.83.

Other methyl esters of 1-methyl-3-(substituted phenyl)pyrazole carboxylic acid and the corresponding free acids produced by hydrolysis of the methyl esters prepared by the procedure of Examples 2-4 include the following:

Methyl 1-methyl-3-(3-chlorophenyl)pyrazole-5-carboxylate, an oil, had the following elemental analysis.

Calculated: C, 58.99; H, 4.95; N, 10.58. Found: C, 59.25; H, 4.88; N, 10.70.

1-Methyl-3-(3-chlorophenyl)pyrazole-5-carboxylic acid; melting point 164°-7° C. (benzene/hexane); yield about 3 g. (from 7.6 g. of pyruvate ester starting material).

Calculated: C, 55.83; H, 3.83; N, 11.84. Found: C, 56.04; H, 3.73; N, 12.04.

Ethyl 1-methyl-3-(3,4-dichlorophenyl)pyrazole-5-carboxylate; melting point=122°-4° C. (hexane).

Calculated: C, 52.73; H, 3.06; N, 9.46. Found: C, 52.47; H, 3.27; N, 9.30.

1-Methyl-3-(3,4-dichlorophenyl)pyrazole-5-carboxylic acid; melting point=252°-6° C. (ethanol).

Calculated: C, 48.73; H, 2.97; N, 10.36. Found: C, 48.65; H, 2.94; N, 10.55.

Methyl 1-methyl-3-(4-methoxyphenyl)pyrazole-5-carboxylate; melting point=76°-78° C.; weight=3.4 g. (from 5.9 g. of pyruvate ester starting material).

Calculated: C, 63.40; H, 5.73; N, 11.38. Found: C, 63.16; H, 5.55; N, 11.24.

1-Methyl-3-(4-methoxyphenyl)pyrazole-5-carboxylic acid: melting point=190°-3° C. (ethanol).

Calculated: C, 62.06; H, 5.21; N, 12.06. Found: C, 62.27; H, 5.24; N, 12.01.

Methyl 1-methyl-4-(4-chlorophenyl)pyrazole-5-carboxylate: melting point=103°-5° C.

Calculated: C, 57.50; H, 4.42; N, 11.17. Found: C, 57.27; H, 4.46; N, 10.90.

1-Methyl-3-(4-chlorophenyl)pyrazole-5-carboxylic acid; melting point=240°-2° C. with decomposition Calculated: C, 55.83; H, 3.83; N, 11.84. Found: C, 56.00; H, 3.70; N, 11.76.

Methyl 1-methyl-3-(3-bromophenyl)pyrazole-5-carboxylate: melting point=95°-7° C.

Calculated: C, 48.84; H, 3.76; N, 9.49. Found: C, 48.90; H, 3.58; N, 9.41.

1-Methyl-3-(3-bromophenyl)pyrazole-5-carboxylic acid; melting point=166°-9° C. (ethanol); yield 3.6 g. (from 11.4 g. of pyruvate acid ester).

Calculated: C, 47.00; H, 3.23; N, 9.97. Found: C, 47.11; H, 3.25; N, 10.13.

Methyl 1-methyl-3-(3,4-dimethyoxyphenyl)pyrazole-5-carboxylate; melting point=133°-5° C. (benzene/hexane)

Calculated: C, 60.86; H, 5.84; N, 10.14. Found: C, 60.97; H, 5.59; N, 10.16.

1-Methyl-3-(3,4-dimethyoxyphenyl)pyrazole-5-carboxylic acid; melting point=189°-91° C. (ethyl acetate/benzene/hexane).

Calculated: C, 59.54; H, 5.38; N, 10.68. Found: C, 59.78; H, 5.22; N, 10.65.

Methyl 1-methyl-3-(m-tolyl)pyrazole-5-carboxylate.

Calculated: C, 67.81; H, 6.13; N, 12.17. Found: C, 67.60; H, 6.26; N, 11.88.

Yield=9.2 g. of yellow oil (from 17.0 g. of pyruvate ester).

1-Methyl-3-(m-tolyl)pyrazole-5-carboxylic acid; melting point=150°-3° C. (from benzene).

Calculated: C, 66.65; H, 5.59; N, 12.96. Found: C, 66.42; H, 5.38; N, 13.22.

EXAMPLE 5

Preparation of
1-Methyl-3-(3-bromophenyl)-4-chloropyrazole-5-carboxylic acid

A reaction mixture was prepared from 13.5 g. of methyl 1-methyl-3-(3-bromophenyl)pyrazole-5-carboxylate and 6.2 g. of sulfuryl chloride in benzene solution. The reaction mixture was heated to refluxing temperature for about 36 hours, and was then cooled and poured into water. The aqueous mixture was extracted with ethyl acetate, and the ethyl acetate extract separated and dried. Removal of the ethyl acetate in vacuo yielded, as a residue, methyl 1-methyl-3-(3-bromophenyl)-4-chloropyrazole-5-carboxylate formed in the above reaction. Recrystallization of the residue from hexane yielded crystalline material melting at 91°-3° C.

Calculated: C, 43.73; H, 3.06; N, 8.50. Found: C, 44.03; H, 3.03; N, 8.55.

Seven and six-tenths grams of the above methyl ester were hydrolyzed in dilute sodium hydroxide by the procedure of Example 1 and the free acid thus produced isolated by the procedure of the same example. Recrystallization of 1-methyl-3-(3-bromophenyl)-4-chloropyrazole-5-carboxylic acid thus prepared from ethanol yielded crystalline material melting at 200°-1° C.

Calculated: C, 41.87; H, 2.56; N, 8.88. Found: C, 42.06; H, 2.38; N, 8.87.

EXAMPLE 6

Preparation of 1-Methyl-3-(3-trifluoromethylphenyl)-4-chloropyrazole-5-carboxylic acid A solution was prepared by dissolving 5.2 g. of methyl 1-methyl-3-(3-trifluoromethylphenyl)pyrazole-5-carboxylate in 200 ml. of glacial acetic acid. The solution was heated to refluxing temperature while gaseous chlorine was passed into the mixture. After about four hours, the addition of chlorine was stopped and the reaction mixture poured over ice. The consequent aqueous mixture was extracted with two 150 ml. portions of chloroform and the chloroform extracts separated, combined and dried. Removal of the chloroform in vacuo yielded as a residue methyl 1-methyl-3-(3-trifluoromethylphenyl)-4-chloropyrazole-5-carboxylate formed in the above reaction. The residue was dissolved in ethyl acetate and the ethyl acetate solution washed with saturated aqueous sodium bicarbonate. The ethyl acetate solution was then dried with phase separation paper. Removal of the solvent in vacuo left a residue which was dissolved in hexane and chromatographed over grade 62 silica. The chromatogram was developed with chloroform/hexane mixtures as the eluant. Use of 100% chloroform as the eluant yielded a small amount of a rapidly moving material which was not the desired product. The desired product, methyl 1-methyl-3-(3-trifluoromethylphenyl)-4-chloropyrazole carboxylate, was next eluted. Fractions containing this material were combined and the chloroform removed in vacuo. Recrystallization of the residue (weight 1.5 g.) from hexane yielded methyl 1-methyl-3-(3-trifluoromethylphenyl)-4-chloropyrazole-5-carboxylate; melting point=97°-8° C. The compound has the following elemental analysis.

Calculated: C, 44.22; H, 2.57; N, 7.93; Cl, 20.08. Found: C, 44.17; H, 2.33; N, 7.99; Cl, 20.36.

The nmr was in agreement with that to be expected from a compound of the given structure.

The methyl ester thus prepared was hydrolyzed with dilute sodium hydroxide according to the procedure of Example 1. The hydrolysis mixture was acidified and the resulting free acid collected by filtration. Recrystallization from an ethanol/water solvent mixture yielded 1-methyl-3-(3-trifluoromethylphenyl)-4-chloropyrazole-5-carboxylic acid melting at 180°-3° C.; yield=700 mg.

Analysis Calculated: C, 47.21; H, 2.65; N, 9.20. Found: C, 47.22; H, 2.79; N, 9.11.

Following the above procedure, the same methyl ester was brominated in refluxing acetic acid. Methyl 1-methyl-3-(3-trifluoromethylphenyl)-4-bromopyrazole-5-carboxylate thus formed was purified by chromatography over silica gel using methylene dichloride as the eluant. 3.0 g. of 1-methyl-3-(3-trifluoromethylphenyl)-4-bromopyrazole-5-carboxylic acid were obtained (from 8.0 g. of unbrominated ester starting material). The ester was hydrolyzed by the procedure of Example 1 using dilute aqueous sodium hydroxide in aqueous ethanol and the free acid isolated by acidification of the hydrolysis mixture. Recrystallization of the free acid ethanol yielded 1-methyl-3-(3-trifluoromethylphenyl)-4-bromopyrazole-5-carboxylic acid melting at 182°-4° C.

Analysis Calculated: C, 41.29; H, 2.31; N, 8.02. Found: C, 41.34; H, 2.45; N, 8.08.

EXAMPLE 7

Preparation of 1,4-Dimethyl-3-phenylpyrazole-5-carboxylic acid

A reaction mixture was prepared from 8.2 g. of methyl 3-benzoyl-2-oxobutanoate, 3 ml. of methyl hydrazine and 50 ml. of methanol. The reaction mixture was heated to refluxing temperature until the reaction was substantially complete and was then cooled. The solvent was removed by evaporation in vacuo. The residue, comprising a mixture of methyl 1,4-dimethyl-3-phenylpyrazole-5-carboxylate and methyl 1,4-dimethyl-5-phenylpyrazole-3-carboxylate, was chromatographed over silica gel using methylene dichloride as the eluant. The first fraction to come off the column comprised the desired methyl 1,4-dimethyl-3-phenylpyrazole-5-carboxylate. Fractions containing this compound were combined and the solvent removed. Hydrolysis of the residue thus obtained with dilute aqueous sodium hydroxide by the procedure of Example 1 yielded the free acid. Recrystallization of the free acid from ethanol gave crystalline 1,4-dimethyl-3-phenylpyrazole-5-carboxylic acid melting at 161°-3° C.

Analysis Calculated: C, 66.65; H, 5.59; N, 12.96. Found: C, 66.81; H, 5.39; N, 12.76.

EXAMPLE 8

Preparation of 1-Methyl-3-(3-trifluoromethylphenyl)-4-aminopyrazole-5-carboxylic acid A solution was prepared by dissolving 40 g. of methyl 3-trifluoromethylbenzoylpyruvate in 300 ml. of methanol. $N_2O_3$ Gas was slowly passed into the solution over a period of four hours (until all of the ester had dissolved plus one additional hour). $N_2O_3$ gas was generated by the dropwise addition of 12N aqueous hydrochloric acid into an aqueous slurry of sodium nitrite. Next, the solvent was removed from the reaction mixture and 200 ml. of water added to the residue. The aqueous mixture was extracted with three 300 ml. portions of ether. The ether extracts were separated, combined and the combined extracts dried. The ether was removed in vacuo leaving as a residue methyl 4-(3-trifluoromethylphenyl)-2,4-dioxo-3-oximinobutanoate formed in the above reaction.

That compound, without further purification, was dissolved in 300 ml. of 1N aqueous hydrochloric acid. The acidic solution was cooled to about 5° C. A solution of 8 ml. of methyl hydrazine in 50 ml. of water was added slowly. Two hours after the addition had been completed, the reaction mixture was extracted with two 300 ml. portions of cold ethyl acetate. The extracts contained a mixture of methyl 1-methyl-3-(3-trifluoromethylphenyl)-4-nitrosopyrazole-5-carboxylate and methyl 1-methyl-5-(3-trifluoromethylphenyl)-4-nitroso-3-carboxylate formed in the above reaction. The ethyl acetate extracts were mixed with 600 ml. of water. Solid sodium dithionite in excess was added thereto in small portions. The initial green-blue solution turned rust brown after about one hour at which time between 150–200 g. of sodium dithionite had been added. The organic and aqueous phases were separated and the aqueous phase extracted with ethyl acetate. The two acetate phases were combined and dried using phase separation paper. Removal of the solvent in vacuo left a mixture of methyl 1-methyl-3-(3-trifluoromethylphenyl)-4-aminopyrazole-5-carboxylate and methyl 1-methyl-5-(3-trifluoromethylphenyl)-4-aminopyrazole-3-carboxylate formed in the above reduction. The mixture of esters was dissolved in chloroform and chromatographed over grade 62 silica. The first major component to be eluted was rechromatographed over silica using hexane containing increasing amounts of ethyl acetate as the eluant. Methyl 1-methyl-3-(3-trifluoromethylphenyl)-4-aminopyrazole-5-carboxylate was eluated with 2% and 4% ethyl acetate in hexane. Yield=1.4 g.

The ester (1.4 g.) was hydrolyzed by the procedure of Example 1 and the free acid isolated by filtration after acidification of the hydrolysis mixture. 1-Methyl-3-(3-trifluoromethylphenyl)-4-aminopyrazole-5-carboxylic acid thus prepared melted at about 172° C. with decomposition after recrystallization from a benzene/hexane solvent mixture; yield—0.7 g.

Analysis Calculated: C, 50.53; H, 3.53; N, 14.73. Found: C, 50.30; H, 3.71; N, 14.47.

EXAMPLE 10

Preparation of 1-Methyl-3-phenyl-4-hydroxypyrazole-5-carboxylic acid

Following the procedure of *Tetrahedron Letters*, 1591 (1971), 0.92 g. of sodium were added to 40 ml. of ethanol. A solution of 0.2 M of the N-methyl-N-carbomethoxymethylhydrazone of methyl benzoylformate in 40 ml. of ethanol were added and the resulting mixture was heated to reflux temperature with stirring for about 2 hours. The ethanol was then removed in vacuo. Water was added and the reaction mixture neutralized by the addition of dilute aqueous sulfuric acid. The acidic solution was extracted with ether and the ether extract dried. The ether was removed in vacuo. The resulting gray solid residue comprising methyl 1-methyl-3-phenyl-4-hydroxypyrazole-5-carboxylate formed in the above reaction melted at 88°–90° C. after recrystallization from hexane. Analysis Calculated: C, 63.40; H, 5.73, N, 11.38. Found: C, 63.57; H, 5.72; N, 11.52.

nmr was in accordance with the proposed structure.

One and two-tenth grams of the above ester was treated with 1 g. of sodium hydroxide in 30 ml. of 50% aqueous ethanol. The hydrolysis mixture was heated at about 80° C. for one hour and was then allowed to cool. The cooled reaction mixture was next made acidic by the addition of dilute aqueous sulfuric acid and the resulting solid, comprising 1-methyl-3-phenyl-4-hydroxypyrazole-5-carboxylic acid, was collected by filtration. The solid melted at 180°–2° C. with decomposition. Recrystallization from a benzene/hexane solvent mixture yielded crystalline material melting at 183°–6° C.

Analysis Calculated: C, 65.34; H, 4.98; N, 13.85. Found: C, 65.55; H, 5.00; N, 14.11.

Following the above procedure, the N-methyl-N-carbomethoxymethylhydrazone of methyl 3-trifluoromethylbenzoylformate was cyclized in the presence of sodium ethoxide to yield methyl 1-methyl-3-(3-trifluoromethylphenyl)-4-hydroxypyrazole-5-carboxylate melting at 101°–3° C. (77% yield based on starting material)

Analysis Calculated: C, 53.51; H, 4.17; N, 8.91. Found: C, 53.39; H, 3.98; N, 8.83.

Still following the above procedure, the ester was hydrolyzed with sodium hydroxide in aqueous ethanol to yield 1-methyl-3-(3-trifluoromethylphenyl)-4-hydroxypyrazole-5-carboxylic acid melting at 192–4° C. The proposed structure was confirmed by nmr.

EXAMPLE 11

Preparation of 3(5)-(3-Trifluoromethylphenyl)-4-hydroxypyrazole-5(3)-carboxylic acid Following the procedure of Example 9, 0.7 g. of sodium was dissolved in 50 ml. of ethanol. A solution of 0.2 M. of the N-carboethoxymethylhydrazone of methyl 3-trifluoromethylbenzoyformate in 40 ml. of ethanol was added. (The ethanol solution was filtered hot prior to addition). The reaction mixutre was stirred at reflux temperature for about two hours after which time the ethanol was removed in vacuo. Water was added followed by 5 ml. of 6N aqueous sulfuric acid, thus making the reaction mixture slightly acidic. Methyl 3(5)-(3-trifluoromethylphenyl)-4-hydroxypyrazole-5(3)-carboxylate formed in the above reaction was insoluble in the acidic aqueous layer and separated. The separated compound was extracted with chloroform and the chloroform extract dried. Removal of the chloroform in vacuo left a dark residue which was purified by chromatography over grade 62 silica using a mixture of methylene dichloride and ethyl acetate as the eluant. After some fast moving materials had been eluted, the desired ester was eluted and yield a solid melting at 177°–8° C. upon evaporation of the eluant; yield=0.3 g.

Analysis Calculated: C, 52.01; H, 3.69N, 9.33. Found: C, 51.77; H, 3.74; N, 9.45.

The ester was hydrolyzed by the procedure of Example 9 to yield 3(5)-(3-trifluoromethylphenyl)-4-hydroxypyrazole-5(3)-carboxylic acid melting at 215°–16° C. with decomposition after recrystallization from aqueous ethanol.

Analysis Calculated: C, 48.54; H, 2.59; N, 10.29. Found: C, 48.44; H, 2.65; N, 10.20.

Following the above procedure, the N-carboethoxymethlhydrazone of methyl benzoylformate was cyclized with sodium ethoxide to yeild methyl 3(5)-phenyl-4-hydroxypyrazole-5(3)-carboxylate. Hydrolysis of this ester by the procedure of Example 10 yielded the corresponding free acid which was isolated by acidification of the hydrolysis mixture. The acid melted at 214°–44° C. with decomposition after recrystallization from a methanol water solvent mixture. Yield 2.3 g. from 3.0 g. of ester. 3(5)-phenyl-4-hydroxypyrazole-5-

(3)-carboxylic acid thus prepared had the following analysis.

Analysis Calculated: C, 63.83; H, 4.29; N, 14.89. Found C, 64.10; H, 4.08; N, 14.91.

As previously stated, the compounds of formulas Ia, Ib, and Ic and their pharmaceutically-acceptable salts and esters are xanthine oxidase inhibitors. Since uric acid is produced by the oxidation of, first, hypoxanthine to xanthine and, second, of xanthine to uric acid via the enzyme, xanthine oxidase, an inhibitor of xanthine oxidase in viv would obviously decrease the uric acid concentrations in the blood. Thus all compounds which inhibit xanthine oxidase in vitro or in vivo are potential anti-gout drugs.

An in vitro xanthine oxidase assay was carried out according to the procedure of Kalckar, *J. Biol. Chem.*, 167, 429 (1947). Xanthine oxidase activity was measured at room temperature by the rate of uric acid formation from xanthine substrate. In a total volume of 1 ml., the incubation mixture contained 50 micromoles of potassium phosphate buffer at pH 7.4, 0.05 micromoles of xanthine and 0.01 units of enzyme preparation (chromatographically purified milk xanthine oxidase, grade III, obtained from Sigma Chemical Company, St. Louis, Missouri). The absorbence change at 292 nm was recored by a Gilford recording spectrophotometer and the uric acid formed was calculated using an extinction coefficient of 12 $mM^{-1} cm^{-1}$ at 292 nm. The results of these assays are set forth in Tables I–III, which follow. Each table carries a structural formula at the head and the left-hand column in each table indicates the particular variations in the structural formula, while the right-hand column gives the concentration of drug in nanograms per ml. which inhibits 50% of the oxidation of xanthine to uric acid by the xanthine oxidase preparation.

TABLE I

| R | $R^1$ | $I_{50}$ (nanograms/ml) |
|---|---|---|
| 3-CF$_3$ | H | 7 |
| 4-OCH$_3$ | H | 72 |
| 3-Cl | H | 72 |
| 4-Cl | H | 400 |
| 3-Br | H | 20 |
| 3-OCH$_3$ | 4-OCH$_3$ | 64 |
| 3-Cl | 4-Cl | 48 |
| 3-CH$_3$ | H | 300 |
| 4-CF$_3$ | H | 115 |
| 4-Br | H | 117 |

TABLE II

| R | X | $I_{50}$ (nanograms/ml) |
|---|---|---|
| Br | Cl | 21 |

TABLE II-continued

| R | X | $I_{50}$ (nanograms/ml) |
|---|---|---|
| CF$_3$ | H | 7 |
| CF$_3$ | OH | 8 |
| CF$_3$ | Br | 20 |
| CF$_3$ | NH$_2$ | 8.6 |
| CF$_3$ | Cl | 14 |

TABLE III

| R | X | $I_{50}$ (nanograms/ml) |
|---|---|---|
| 4-OMe | OH | 170 |
| 4-F | OH | 350 |
| 3-CF$_3$ | H | 100 |
| 3-CF$_3$ | OH | 12.2 |

Compounds corresponding to formulas Ia, Ib and Ic above are active in vivo in lowering plasma uric acid levels. Two different experimental methods were used to determine in vivo activity but both methods gave comparable results. The first method, the spectrofluorometric method, was modified from the precedure of Sumi et al., *Clinica. Chimica. Acta.*, 73, 233 (1976). Rats were sacrificed by decapitation and their blood collected into vacutainer tubes containing heparin via heparinized glass funnels. The blood was centrifuged for 8 minutes at 4000 rpm after which time the plasma was separated and diluted 1:1 with water. Plasma protein was precipitated by addition of acetic acid to a final concentration of 0.007 molar and boiling the resulting mixture for 5 minutes in Sorval tubes. Clear deprotein plasma was obtained after centrifugation of the resulting plasma for 30 minutes at 25,000 rpm. Uric acid was assayed as follows: 0.2 ml. aliquots of the clear deproteinized plasma were mixed with 120 λ of uricase (0.045 mu/ml.) and incubated for 30 minutes at 27° C. 1.0 ml. of a p-hydroxyphenylacetic acid buffer was added. Samples obtained from feeding rats or dogs serial doses of the compound under test were incubated with the above buffer solution for 30 minutes at 27° C. Fluoroescence of the solution was measured in quartz tubes using an Aminco Bowman-Spectrofluorimeter having excitation of 321 nm and emission at 412 nm. Five uric acid standards from 6–30 micromolar were assayed for each test and each standard yielded a linear curve.

The second method is called the HPLC-EC Detection method. In this procedure, blood plasma was collected from rats as described above and from dogs in heparinized syringes from the cefalic vein in the forearm. The blood plasma was centrifuged with Sure-Sep to separate plasma. Deproteinized plasma was prepared in each instance by first diluting one volume of plasma with one volume of an internal standard solution, 4 mcg./ml., and then addition of two volumes of 5% trichloroacetic acid. Standards were added to control plasma in the range of 0-8 mcg./ml. of uric acid. Samples obtained by feeding graded doses of the drug under test to dogs or rats were mixed for 30 seconds and then centrifuged in an Eppendorf microcentrifuge. Supernates were diluted 1:10 in column buffer and assayed for uric acid. Internal standards used were 3-methyluric acid for the rat samples and 3,9-dimethyluric acid for dog samples. Assays were performed as follows using a Bioanlaytic Systems Inc. LC-44 analyser and an electrochemical detector system based on an Altex model 110 pump coupled with a CP-O carbon paste electrodetector. Samples for assay were put into a DuPont 834 autosampler and automatically injected into a laboratory packed stainless steel column (4.1 mm id, ¼″ od 25 cm.1) containing reverse phase packing (sperisorb. O.D. 5μ, Regis Chemical Co.). The column buffers employed were 0.1 M disodium phosphate, 0.05 M citric acid and 10% methanol for rat samples; 0.1 M disodium phosphate, 10% methanol and citric acid titrated at pH 6.5 for dog samples. The same internal standards were employed as before. Retention times for uric acid, 3-methyluric acid and 3,9-dimethyluric acid were established. Uric acid levels were then calculated from peak areas by computer analysis. Table IV which follows gives the oral $ED_{50}$ in rats for a group of the preferred compounds of this invention (those in which the 3-position of the pyrazole ring carries a 3-trifluormethylphenyl group). In tis table, column 1 gives the substituent at C-4 of the pyrazole ring and column 2 the $ED_{50}$ in mg. per kg. (that dose which reduces plasma level of uric acid by one-half).

The compounds represented by the above formula are also relatively non-toxic. In column 3 of Table IV are listed the oral $LD_{50}$ for mice in mg. per kg. (with standard error) for each of the compounds of column 1 (dose which kills one-half of the animals). Finally, column 4 in Table IV gives the ratio of $LD_{50}$ to $ED_{50}$. It will be seen that the ratio of the $LD_{50}$ to the $ED_{50}$ is quite high, giving a substantial margin of safety for using the compounds of formulas Ia, Ib, and Ic in treating gout in mammals, particularly humans.

Other compounds represented by formulas Ia, Ib and Ic above are also active in vivo inhibitors of xanthine oxidase. Table V which follows gives results obtained by oral administration in rats. In the table, column 1 gives the acid derivative, column 2 the dosage and column 3, the percent inhibition.

TABLE IV

| X | $ED_{50}$ mg/kg | $LD_{50}$ mg/kg | Ratio |
|---|---|---|---|
| $NH_2$ | 23 | — | — |
| Cl | 8.5 | 322 ± 38 | 38 |
| H | 30 | 585 ± 45 | 19.5 |
| Br | 11 | 300–500 | 27–45 |

TABLE V

| R | Oral Dosage mg·kg | Percent Inhibition |
|---|---|---|
| $OCH_3$ | 24 | 50 |
| $NH_2$ | 90 | 23.5 |

The compounds of formulas Ia, Ib and Ic above are all active by the oral route, and are preferably formulated in solid form for oral administration. For example, a tablet containing from 100 to 250 mg. of a compound according to formulas Ia, Ib or Ic would, for example, contain also per tablet 38 mg. starch, 25 mg. lactose, 2 mg. ethylcelluose, 7 mg. alginic acid, 1 mg. magnesium steareate and 2 mg. of talc. A formulation utilizing capsules would, for instance, contain per capsule from 100 to 250 mg. or 500 mg of the drug, and, for example, 48 mg. of lactose and 2 mg. of magnesium stearate. Solid formulations for loading into capsules can be prepared with 600 or even 800 mg. of drug per dose if the drug is first densified. For parenteral administration, only acids or pharmaceutically-acceptable salts thereof can be employed. If an acid is employed, it should be neutralized, for instance with 10% sodium hydroxide, and the resulting solution mixed with an isotonic salt solution. Preferably, a salt is employed and simply added to the isotonic salt solution in the desired injection volume.

The compounds of formula Ia, Ib and Ic above are useful in lowering blood urate (uric acid) levels to within normal limits and thus are of value in the chemotherapy of hyperuricaemic conditions such as gout and gouty arthritis, particularly when that disease is caused predominately by abnormalities in purine metabolism.

We claim:

1. A method for lowering the blood urate (uric acid) level in mammals which comprises the parenteral administration to a mammal having an elevated blood urate level and in need of treatment a drug of the formula

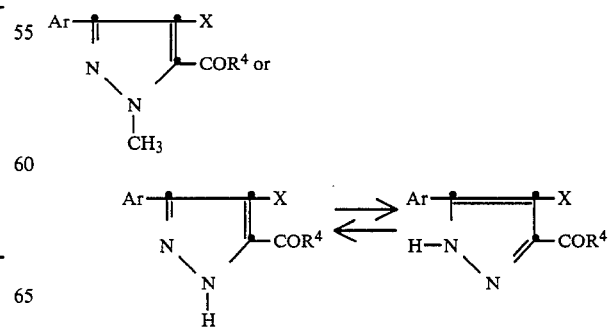

wherein Ar is

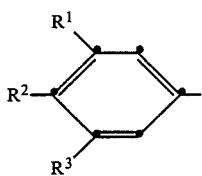

wherein
 $R^1$, $R^2$ and $R^3$ are individually H, Cl, Br, F, I, $C_{1-3}$ alkyloxy or $C_{1-3}$ haloalkyl; provided that at least one of $R^1$, $R^2$ and $R^3$ is H and one is other than H, and only one is I;
 X is $NH_2$, OH, H, F, Cl, Br, I or $C_{1-3}$ alkyl;
 $R^4$ is OH or OM; wherein M is a non-toxic cation; in a quantity sufficient to lower said elevated blood urate level.

2. A method for lowering the blood urate (uric acid) level in mammals which comprises the oral administration to a mammal having an elevated blood urate level and in need of treatment an amount of a drug of the formula

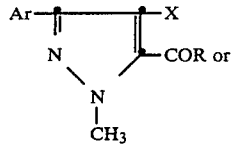

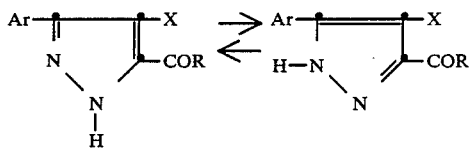

wherein Ar is

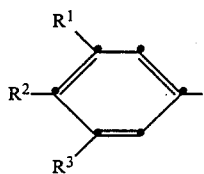

wherein
 $R^1$, $R^2$ and $R^3$ are individually H, Cl, Br, F, I, $C_{1-3}$ alkyloxy; provided that at least one of $R^1$, $R^2$ and $R^3$ is H, one is other than H and only one is I;
 X is $NH_2$, H, OH, Cl, F, Br, I or $C_{1-3}$ alkyl;
 R is OH, OM, O-alk, $NH_2$, NH-alk or $N(alk)_2$; wherein alk is $C_{1-5}$ alkyl; and M is a non-toxic cation; in an amount sufficient to lower said blood urate levels.

3. A method according to claim 2 in which, in the administered drug, Ar is

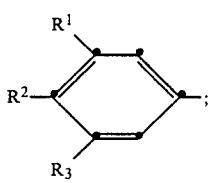

both $R^2$ $R^3$ are H and $R^1$ is $CF_3$, Cl, Br, R or $CH_3O$.

4. A compound of the group 1-methyl-3-(3-trifluoromethylphenyl)-4-aminopyrazole-5-carboxylic acid, 1-methyl-3-(3-bromophenyl)-4-chloropyrazole-5-carboxylic acid, 1-methyl-3-(3-trifluoromethylphenyl)-4-hydroxypyrazole-5-carboxylic acid, 1-methyl-3-(3-trifuoromethylphenyl)-4-bromopyrazole-5-carboxylic acid, 1-methyl-3-(3-bromophenyl)pyrazole-5-carboxylic acid, 1-methyl-3-(3-trifluoromethylphenyl)-4-chloropyrazole-5-carboxylic acid, 1-methyl-3-(3-trifluoromethylphenyl)-pyrazole-5-carboxylic acid, and 3(5)-(3-trifluoromethylphenyl)-4-hydroxypyrazole-5(3)-carboxylic acid.

5. A compound of the formulas

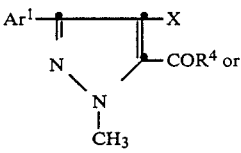

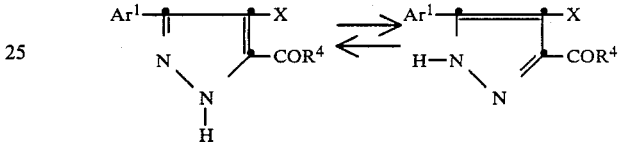

wherein $Ar^1$ is 3-trifluoromethylphenyl, X is OH, $NH_2$, H, Br, Cl, F or I and $R^4$ is OH or OM wherein M is a non-toxic cation.

6. A method according to claim 2 in which a compound according to claim 4 is administered.

7. A method according to claim 2 in which a compound according to claim 5 is administered.

8. A method according to claim 2 in which, in the administered drug, the radical Ar is a 3-trifluoromethylphenyl radical.

9. A method according to claim 2 in which, in the administered drug, X is H, OH, Br, Cl or $NH_2$.

10. A method according to claim 9 in which X is H.

11. A method according to claim 9 in which X is OH.

12. A method according to claim 2 in which, in the administered drug, the radical $R^4$ is OH.

13. A method according to claim 1 in which, in the administered drug, $R^4$ is OM and M is an alkali metal cation.

14. A method according to claim 2 in which 1-methyl-3-(3-trifluoromethylphenyl)-4-chloropyrazole-5-carboxylic acid or a salt thereof with a non-toxic cation is administered.

15. A method according to claim 2 in which 1-methyl-3-(3-bromophenyl)-pyrazole-5-carboxylic acid or a salt thereof with a non-toxic cation is administered.

16. A method according to claim 2 in which 1-methyl-3-(3-trifluoromethylphenyl)-4-hydroxypyrazole-5-carboxylic acid or a salt thereof with a non-toxic cation is administered.

17. A method according to claim 2 in which 1-methyl-3-(3-trifluoromethylphenyl)-4-bromopyrazole-5-carboxylic acid or a salt thereof with a non-toxic cation is administered.

18. A method according to claim 2 in which 3(5)-(3-trifluoromethylphenyl)-4-hydroxypyrazole-5(3)-carboxylic acid or a salt thereof with a non-toxic cation is administered.

19. A method according to claim 2 in which 1-methyl-3-(3-trifluoromethylphenyl)pyrazole-5-carboxylic acid or a salt thereof with a non-toxic cation is administered.

20. A method according to claim 2 in which 1-methyl-3-(3-trifluoromethylphenyl)-4-aminopyrazole-5-carboxylic acid or a salt thereof with a non-toxic cation is administered.

21. A method according to claim 2 in which 1-methyl-3-(3-bromophenyl)-4-chloropyrazole-5-carboxylic acid or a salt thereof with a non-toxic cation is administered.

22. A method according to claim 1 in which a pyrazole of the formula is administered.

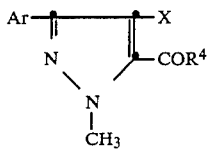

23. A method according to claim 2 in which a pyrazole of the formula is administered.

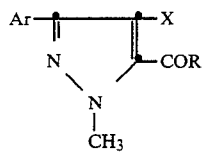

24. A compound according to claim 5 said compound having 1-methyl-3-(3-trifluoromethylphenyl)-4-aminopyrazole-5-carboxylic acid.

25. A compound according to claim 5 said compound being 1-methyl-3-(3-bromophenyl)pyrazole-5-carboxylic acid.

26. A compound according to claim 5 said compound being 1-methyl-3-(3-trifluoromethylphenyl)-4-hydroxypyrazole-5-carboxylic acid.

27. A compound according to claim 5 said compound being 1-methyl-3(3-trifluoromethylphenyl)-4-bromopyrazole-5-carboxylic acid.

28. A compound according to claim 5 said compound being 1-methyl-3-(3-trifluoromethylphenyl)-pyrazole-5-carboxylic acid.

29. A compound according to claim 5 said compound being 3(5)-(3-trifluoromethylphenyl)-4-hydroxypyrazole-5(3)-carboxylic acid.

30. A compound according to claim 5, said compound being 1-methyl-3-(3-bromophenyl)-4-chloropyrazole-5-carboxylic acid.

31. A compound according to claim 5, said compound being 1-methyl-3-(3-trifluoromethylphenyl)-4-chloropyrazole-5-carboxylic acid.

32. A pharmaceutical formulation according to claim 1 in which the active drug is present in an amount of from 100–500 mg.

33. A formulation according to claim 1 in which the active drug is 1-methyl-3-(3-trifluoromethylphenyl)-4-chloropyrazole-5-carboxylic acid or a nontoxic cationic salt thereof.

34. A formulation according to claim 1 in which the active drug is 1-methyl-3-(3-bromophenyl)-pyrazole-5-carboxylic acid or a nontoxic cationic salt thereof.

35. A formulation according to claim 1 in which the active drug is 1-methyl-3-(3-trifluoromethylphenyl)-4-hydroxypyrazole-5-carboxylic acid or a nontoxic cationic salt thereof.

36. A formulation according to claim 1 in which the active drug is 1-methyl-3-(3-trifluoromethylphenyl)-4-bromopyrazole-5-carboxylic acid or a nontoxic cationic salt thereof.

37. A formulation according to claim 1 in which the active drug is 1-methyl-3-(3-trifluoromethylphenyl)-pyrazole-5-carboxylic acid or a nontoxic cationic salt thereof.

38. A formulation according to claim 1 in which the active drug is 3(5)-(3-trifluoromethylphenyl)-4-hydroxypyrazole-5(3)-carboxylic acid or a nontoxic cationic salt thereof.

39. A formulation according to claim 1 in which the active drug is 1-methyl-3-(3-trifluoromethylphenyl)-4-aminopyrazole-5-carboxylic and or a nontoxic cationic salt thereof.

40. A formulation according to claim 1 in which the active drug is 1-methyl-3-(3-bromophenyl)-4-chloropyrazole-5-carboxylic acid or a nontoxic cationic salt thereof.

41. A pharmaceutical formulation according to claim 1 in which the active drug is present in an amount from 100–500 mg.

42. A method of inhibiting the enzyme xanthine oxidase in a mammal which comprises administering to said mammal by the oral route a xanthine oxidase inhibiting dose of a drug of the formula

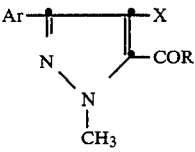

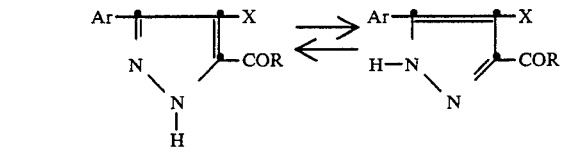

wherein Ar is

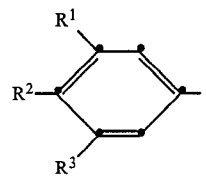

wherein
R$^1$, R$^2$ and R$^3$ are individually H, Cl, Br, F, I, C$_{1-3}$ haloalkyl or C$_{1-3}$ alkyloxy provided that one of R$^1$, R$^2$ and R$^3$ is H, one is other than H and not more than one is I;
X is NH$_2$, H, Cl, Br, F, I, OH or C$_{1-3}$ alkyl;
R is OH, OM, O-alk, NH$_2$, NH-alk or N(alk)$_2$; wherein alk is C$_{1-5}$ alkyl; and M is a non-toxic cation.

43. A method according to claim 2 in which, in the administered drug, R$^4$ is OM and M is an alkali metal cation.

44. A xanthine oxidase inhibiting composition in unit dosage form adapted for oral administration consisting of per unit dosage an amount of a drug according to claim 4 or a non-toxic cationic salt thereof sufficient to lower blood urate levels plus one or more pharmaceutical excipients.

45. A xanthineoxidase inhibiting composition in unit dosage form adapted for parenteral administration consisting of per unit dosage an amount of a drug according to claim 4 or a non-toxic cationic salt thereof sufficient to lower blood urate levels plus one or more pharmaceutical excipients.

* * * * *